(12) United States Patent
Estes et al.

(10) Patent No.: US 6,758,863 B2
(45) Date of Patent: Jul. 6, 2004

(54) VERTICALLY EXPANDING INTERVERTEBRAL BODY FUSION DEVICE

(75) Inventors: Bradley T. Estes, Memphis, TN (US); Andrew M. Dickson, Gallatin, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/317,660

(22) Filed: Dec. 12, 2002

(65) Prior Publication Data

US 2003/0093154 A1 May 15, 2003

Related U.S. Application Data

(63) Continuation of application No. 09/696,146, filed on Oct. 25, 2000, now abandoned.

(51) Int. Cl.$^7$ ............................................. A61F 2/44
(52) U.S. Cl. ................................. 623/17.16; 623/17.11
(58) Field of Search ........................... 623/13.11, 13.12, 623/13.18, 14.13, 16.11, 17.11–17.16

(56) References Cited

U.S. PATENT DOCUMENTS

| | | | |
|---|---|---|---|
| 4,512,038 A | 4/1985 | Alexander et al. | ............... 3/1.9 |
| 4,645,503 A | 2/1987 | Lin et al. | ............... 623/16 |
| 4,945,127 A | 7/1990 | Kagawa et al. | ............ 524/524 |
| 4,950,258 A | 8/1990 | Kawai et al. | ............... 604/281 |

(List continued on next page.)

FOREIGN PATENT DOCUMENTS

| | | |
|---|---|---|
| EP | 0326426 | 8/1989 |
| EP | 1000958 | 12/1998 |
| FR | 2712486 | 5/1995 |
| FR | 2718634 | 10/1995 |
| WO | WO 97/09007 | 3/1997 |
| WO | WO 98/38918 | 9/1998 |
| WO | WO 00/25706 | 5/2000 |
| WO | WO 00/44319 | 8/2000 |
| WO | WO 00/59412 | 10/2000 |

OTHER PUBLICATIONS

Blanchard, C.R., "Biomaterials: Body Parts of the Future," Technology Today, Fall 1995.
Middleton, J.C., Tipton, A.J., "Synthetic Biodegradable Polymers as Medical Devices," Medical Plastics and Biomaterials Magazine, Mar. 1998.

Primary Examiner—David J. Isabella
Assistant Examiner—Hieu Phan
(74) Attorney, Agent, or Firm—Woodard, Emhardt, Moriarty, McNett & Henry LLP

(57) ABSTRACT

This invention relates to intervertebral spacers for use in orthopedic treatment of spinal defects. The intervertebral space is formed of a shaped memory polymer material. The spacer can be fabricated into a desired configuration and then deformed into an alternative or deformed configuration. Cooling the deformed spacer effectively freezes the spacer into its deformed conformation. The deformed configuration can be selected to facilitate implantation of the spacer into a prepared disc space between adjacent vertebrae. During operation, the surgeon can heat the spacer to allow it to revert to its original configuration. The spacer in its original conformation is sized to restore and/or maintain the adjacent vertebrae in a desired conformation and disc space height.

39 Claims, 4 Drawing Sheets

U.S. PATENT DOCUMENTS

| | | | |
|---|---|---|---|
| 5,145,935 A | 9/1992 | Hayashi | 528/65 |
| 5,189,110 A | 2/1993 | Ikematu et al. | 525/314 |
| 5,192,326 A | 3/1993 | Bao et al. | 623/17.12 |
| 5,534,028 A | 7/1996 | Bao et al. | 623/17.16 |
| 5,603,713 A | 2/1997 | Aust et al. | 606/61 |
| 5,603,722 A | 2/1997 | Phan et al. | 606/198 |
| 5,607,474 A | 3/1997 | Athanasiou et al. | 623/11 |
| 5,674,286 A | 10/1997 | D'Alessio et al. | 424/423 |
| 5,676,699 A | 10/1997 | Gogolewski et al. | 623/16 |
| 5,716,410 A | 2/1998 | Wang et al. | 623/12 |
| 5,716,416 A | 2/1998 | Lin | 623/17.16 |
| 5,749,916 A | 5/1998 | Richelsoph | 623/17.16 |
| 5,824,093 A | 10/1998 | Ray et al. | 623/17.16 |
| 5,868,745 A | 2/1999 | Alleyne | 606/61 |
| 5,868,746 A | 2/1999 | Sarver et al. | 606/69 |
| 5,919,234 A | 7/1999 | Lemperle et al. | 623/16 |
| 5,954,744 A | 9/1999 | Phan et al. | 606/198 |
| 5,976,186 A | 11/1999 | Bao et al. | 623/17.16 |
| 5,976,187 A | 11/1999 | Richelsoph | |
| 6,017,366 A | 1/2000 | Berman | 623/21 |
| 6,019,793 A | 2/2000 | Perren et al. | 623/17 |
| 6,022,352 A | 2/2000 | Vandewalle | 606/73 |
| 6,024,764 A | 2/2000 | Schroeppel | 623/1 |
| 6,039,761 A | 3/2000 | Li et al. | 623/17 |
| 6,045,579 A | 4/2000 | Hochshuler et al. | 623/17 |
| 6,071,982 A | 6/2000 | Wise et al. | 523/113 |
| 6,090,996 A | 7/2000 | Li | 623/11 |
| 6,093,205 A | 7/2000 | McLeod et al. | 623/17 |
| 6,102,932 A | 8/2000 | Kurz | 606/200 |
| 6,102,933 A | 8/2000 | Lee et al. | 606/109 |
| 6,127,597 A | 10/2000 | Beyar et al. | 623/16 |
| 6,132,465 A | 10/2000 | Ray et al. | 623/17.16 |
| 6,136,031 A * | 10/2000 | Middleton | 623/17.16 |
| 6,156,842 A | 12/2000 | Hoenig et al. | 525/171 |
| 6,160,084 A | 12/2000 | Langer et al. | 528/272 |
| 6,193,757 B1 | 2/2001 | Foley et al. | 623/17.16 |
| 6,206,883 B1 | 3/2001 | Tunc | 606/77 |
| 6,221,075 B1 | 4/2001 | Tormala et al. | 606/77 |
| 6,264,695 B1 * | 7/2001 | Stoy | 623/17.16 |

* cited by examiner

VERTICALLY EXPANDING INTERVERTEBRAL BODY FUSION DEVICE

This is a continuation of application Ser. No. 09/696,146 filed Oct. 25, 2000 now abandoned

BACKGROUND OF THE INVENTION

In general, this invention relates to intervertebral spacers and their use to treat spinal defects. More specifically, the present invention is directed to intervertebral spacers composed of a shape memory polymeric material that can be deformed and converted to a desired configuration to facilitate treatment of spinal defects.

Removal of damaged or diseased discs and implantation of intervertebral spacers into the disc space are known medical procedures used to restore disc space height, treat chronic back pain and other ailments. The spacers can be formed of a variety of materials—both resorbable and non-resorbable materials, including bone-derived material, metallic, ceramic, and polymeric materials. Typically, spacers are pre-formed into a general configuration that is easy to fabricate or, in selected examples, spacers are pre-formed to a generalized configuration that conforms to the vertebral endplates. During surgery, the vertebral endplates must be prepared to receive the spacers. This typically involves either partial or full discectomy to remove the damaged or diseased disc. Thereafter the bone tissue of the vertebral endplates is cut and shaved to receive the spacer. It is also desirable to promote fusion between the vertebral bodies that are adjacent to the damaged or diseased discs. Exposing the cancellous bone tissue in the vertebral body enhances the fusion between the vertebrae. Additionally, an osteogenic material is combined with a spacer—typically packed inside the spacer body and in the disc space around the spacer—to facilitate and promote bone growth.

Preparation of the endplates requires precise cutting to reduce incidences of retropulsion of the preformed spacers and promote bone fusion. The spacers often are designed to interengage the adjacent bony tissue to provide a secure, mechanical interlock with the tissue. A fully seated spinal spacer also helps ensure that any osteogenic material packed into the spacer and surrounding disc space is maintained in intimate contact with the cancellous tissue, which further promotes bone growth. This requires the surgeon to cut the opposing endplates to matingly conform to the upper and lower surfaces of the pre-formed spacers. This can be a very difficult and time-consuming task, and can lead to complications during the operation. It would be preferable to provide a spacer that is self-conforming to the vertebral endplates. However, the implanted spacer must still provide sufficient strength to support the load exerted by the spine without substantial deformation.

To further facilitate implantation of spacers, sufficient clearance between the vertebral bodies must be made available. This is most often accomplished by over-distracting the adjacent vertebrae to provide an enlarged area to work and facilitate implantation of the spacer. While the spacers can be implanted from various directions, including anteriorly, posteriorly and posterior laterally, each of the directions for approach require over-extension of the adjacent vertebrae using distracters. Often a portion of the cortical rim of the upper and lower vertebrae must be cut to provide an entrance into the disc space to insert the spacer. The adjacent vertebrae must be spread apart to provide sufficient room for the surgeon to insert the spacer. This can cause further injury to the already damaged spine. This trauma can also result in over-extension and stretching of associated ligaments and tendons. It would be preferable to reduce over-distraction of the adjacent vertebrae and minimize invasive cutting of the vertebral bodies, yet still be able to insert a spacer sufficient large to restore and maintain a desired disc height.

Thus, in view of the above-described problems, there continues to be a need for advancements in the relevant field, including improved spacers for treatment of spinal defects, methods of fabricating the spacers, and methods of treating spinal defects. The present invention is such an advancement and provides a wide variety of additional benefits and advantages.

SUMMARY OF THE INVENTION

The present invention relates to intervertebral spacers, the manufacture and use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In general, this invention provides an expandable spacer for implantation between adjacent vertebrae to treat spinal defects. The spacer can be formed of a shape member polymer (SMP) material and fabricated into a pre-selected configuration. Fabricating the space using a shape memory polymeric material imparts novel and particularly advantageous characteristics to the intervertebral spacer. In a preferred embodiment, the spacer fabricated from an SMP material can be molded into a desired configuration. Curing the polymeric material imprints the original molded configuration to the spacer body. However, when the spacer body is heated above a deformation temperature ($T_d$)—which is usually equivalent to the glass transition temperature ($T_g$) of the polymeric material—the SMP becomes elastic. When heated to a temperature equal to or above $T_d$, the spacer body can be deformed to a wide variety of configurations by applying pressure or forcing it into a mold. The spacer body can be "frozen" into the deformed configuration by cooling it below the $T_d$ while the body is maintained in the deformed configuration. Thereafter, the deformed spacer body retains the deformed configuration until it is heated above $T_d$. When the spacer body is reheated above $T_d$, the SMP material again becomes elastic; and in the absence of any applied pressure, the spacer body automatically reverts to it original configuration. This process can be repeated any number of times without detrimental effect on the SMP material or the spacer itself.

In one form, the present invention provides a fabricated intervertebral spacer molded to a desired shape and/or size. The spacer comprises a body composed of a polymeric material that exhibits a shape memory defect above a deformation temperature. Above the deformation temperature, the body can be deformed to a first configuration. Preferably, the first configuration provides a reduced external volume or cross-sectional area. Cooling the deformed spacer to a temperature below the deformation temperature, effectively freezes the spacer body in the first configuration. The deformed spacer can then maintain the first configuration until it is desired to cause the body to revert to its original, molded configuration. Most preferably, this occurs after implantation of the deformed spacer into the intervertebral space. Heating the implant spacer above its deformation temperature permits the spacer to revert to its originally molded configuration. Since the deformed spacer can be smaller than the molded spacer, the deformed spacer can be more readily inserted into the disc space using orthoscopic, laparoscopic or other minimally invasive surgical techniques. Additionally, the preferred procedure does not require over-extension of the adjacent vertebral bodies, nor does the preferred procedure require extensive cutting and/or shaping of the cortical rim and vertebral endplates. When desired, preferably after insertion into the disc space, the spacer body is then heated above the deformation temperature. This causes the spacer body to revert to its originally fabricated configuration or a substantially similar configuration.

In one embodiment, the present invention provides an intervertebral spacer for insertion between opposing endplates of adjacent vertebrae. The spacer comprises a body composed of a shaped member polymeric material and has a first upper surface and an opposite lower surface separated from the upper surface by a peripheral sidewall. The body is provided in a first configuration and is capable of being deformed under select stimuli to a second configuration. In the second configuration, the upper plate is adapted to bear against the first endplate of a first vertebra, and the lower surface is adapted to bear against an opposing endplate of an adjacent vertebra.

In another embodiment, the present invention provides an intervertebral spacer for implantation between adjacent vertebrae. The spacer comprising a body having a first bearing surface, an opposite second bearing surface, and a peripheral sidewall therebetween and composed of a shape memory polymeric material, said body capable of withstanding a compressive force of at least 1000 N without significant deformation when maintained at a temperature below a deformation temperature, yet capable of deforming above the deformation temperature.

In still yet another embodiment, the present invention provides a method of orthopedic treatment. The method comprises preparing a disc space between adjacent vertebrae to receive an intervertebral spacer; implanting an intervertebral spacer in the prepared disc space, wherein the spacer is composed of a shape memory polymeric material and is provided in a first configuration exhibiting a first external volume; and subjecting the spacer to a selected stimuli wherein the spacer deforms to a second configuration that exhibits a second external volume greater than the first external volume.

It is one object of the present invention to provide an expanding intervertebral spacer for use in orthopedic treatment.

Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

In general, this invention provides an expandable spacer for implantation between adjacent vertebrae to treat spinal defects. The spacer can be formed of a shape member polymer (SMP) material and molded to a pre-selected configuration. The spacer can then be heated to a deformation temperature and then deformed to provide a deformed spacer. The deformed spacer has a reduced cross-sectional profile that permits it to be readily implanted into a disc space. Implantation of the deformed spacer is less invasive and requires less cutting of the adjacent endplates. In preferred treatment methods, the deformed spacer can be implanted between adjacent vertebrae without requiring cutting or removal of a portion of the cortical rim surrounding the vertebrae. The deformed spacer expands after insertion into the prepared disc space by application of a pre-selected stimuli. The deformed spacer expands to a second configuration that is substantially equivalent to the originally molded configuration. In the expanded configuration, the spacer extends vertically from the upper endplate to the lower endplate, supports the spinal column, and maintains the desired disc space height. In preferred forms, the spacer promotes spinal fusion by serving as a depot for osteogenic material. In yet other forms, the spacer can be used in vertebroplasty to treat crushed or fractured vertebrae. In addition, the molded spacer can be provided in a wide variety of pre-selected shapes with additional external and internal structures. The molded spacers can vary in size. The molded spacers are sized so that they can maintain a desired disc space height between the different vertebral bodies, including: cervical, thoracic, lumbar, and sacral vertebral bodies.

Figure 1:
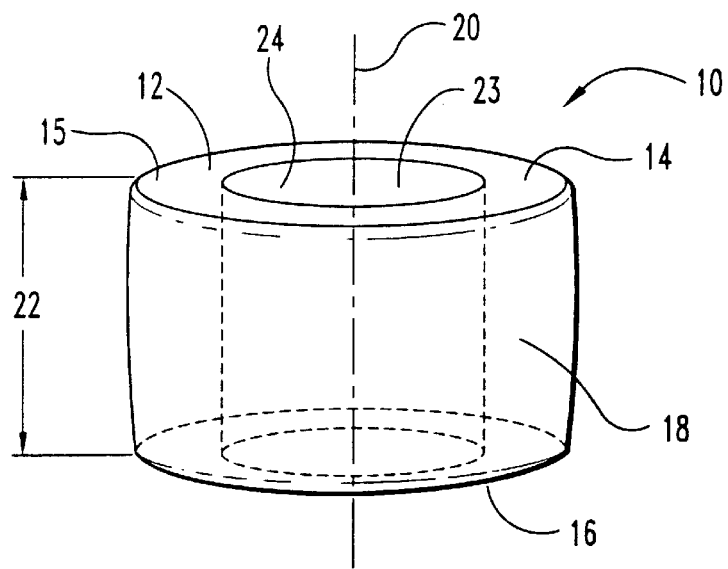
FIG. 1 is a perspective view of one embodiment of a molded spacer for use in the present invention.

FIG. 1 is an illustration of one embodiment of a molded spacer 10 for use in the present invention. Molded spacer 10 includes a body 12 formed of a shape memory polymeric material. Body 12 includes an upper first surface 14 and an opposite lower second surface 16. A peripheral sidewall 18 separates first surface 14 from second surface 16. First and second surfaces 14 and 16 are provided to bear against opposing endplates of adjacent vertebrae. While both first and second surfaces, 14 and 16, are illustrated as substantially planar surfaces, one or both of these surfaces can be provided in alternative forms. Preferably, the alternative forms conform anatomically to the endplates of the respective vertebra. For example, first surface 14 can be molded to exhibit a convex profile. Alternatively, first surface 14 can be molded to resemble only a portion of the respective, opposing endplate. In this regard, a pair of spacers 10 each resembling the mirror image of the other can be implanted together into the disc space. (See for example FIGS. 4 and 5, which depict the bi-lateral placement of a pair of spaces.)

Peripheral sidewall 18 is illustrated as a continuous curved wall encircling body 12. As will be seen in alternative embodiments described below, the peripheral sidewall can include various wall portions, each having it own surface features.

In the illustrated embodiment, body 12 is illustrated as a cylinder concentric about vertical axis 20. Body 12 has a height ($H_1$) along axis 20 and defined by reference line 22. The height $H_1$ of body 12 can be selected to maintain desired disc height between selected vertebrae, including cervical, thoracic, lumbar, and sacral vertebrae. In preferred embodiments, the height of body 12 is selected to be between 2 mm and about 10 mm; more preferably between about 6 mm and about 14 mm. The diameter of body 12 is selected to stabilize the spacer in the disc space and/or to provide optimum efficacy for spinal fusion. The diameter of body 12 measured orthogonal to vertical axis 22 is selected to be between about 5 mm and about 60 mm; more preferably, between about 10 mm and about 40 mm.

Body 12 includes at least one opening 24 extending into interior cavity 23. Cavity 23 serves as a depot for receipt of an osteogenic material to promote spinal fusion between adjacent vertebrae. The size of opening 24 can vary. When opening 24 is located in one or the other bearing surfaces 14 and 16, the remaining surface 15 surrounding the opening is sufficient to bear the compressive force exerted by the spinal column without subsiding into the cancellous bone tissue. Preferably spacer 10 is provided with a compression modulus of elasticity substantially equivalent to that of cortical bone.

Peripheral sidewall 18 can vary in thickness depending upon a number of factors, including: the nature of the polymeric composition, the location or level of the spine that the spacer is intended for use, and the number of spacers intended to be implanted in the same disc space. Generally, the average thickness of peripheral sidewall 18 is selected to between about 0.5 mm and about 4 mm. More preferably, the thickness of peripheral sidewall is between about 2 mm. and about 3 mm.

Figure 2:
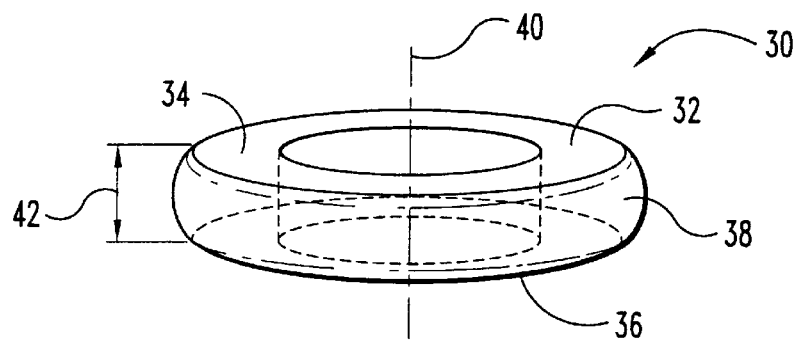
FIG. 2 is a perspective view of one embodiment of a deformed spacer for use in the present invention.
Figure 3:
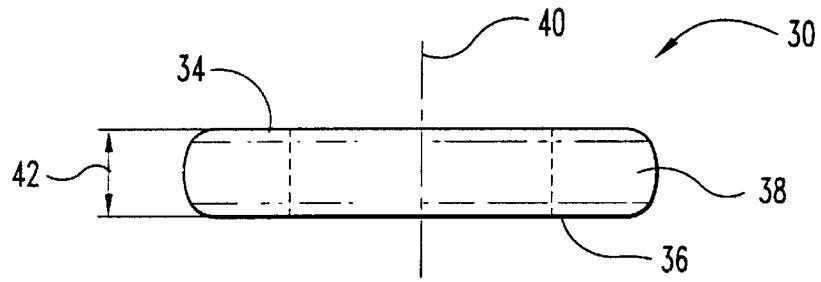
FIG. 3 is a side elevation view of the deformed spacer of FIG. 2.

Referring now to FIGS. 2 and 3, deformed spacer 30 derived from spacer 10 of FIG. 1 is depicted. Heating spacer 10 above a pre-selected or predetermined deformation temperature and applying pressure either along axis 20 or parallel to first surface 14 provides deformed spacer 30. In the illustrated embodiment, deformation of spacer 30 does not substantially change the configuration of spacer body 12 other than compressing the body 12 along axis 22. Therefore, spacer 30, similar to spacer 10, includes a body 32 having an upper, first surface 34 and an opposite, lower, second surface 36. First surface 34 is separated from second surface 36 by a peripheral sidewall 38. The height $H_2$ of deformed spacer 30, and therefore the separation distance between first surface 38 and second surface 36, is represented by reference line 42. The separation of first surface 38 from second surface 36 is substantially smaller than the corresponding separation between first surface 14 and second surface 16 on spacer 10. It can readily be seen from the illustrated embodiment that deformed spacer 30 has a reduced cross-sectional area compared to spacer 10 if sectioned through axis 20. In preferred embodiments, height $H_2$ measured along axis 40 and represented by reference line 42 is at least about 50% shorter than the separation distance, $H_1$, between the surfaces 14 and 16 of spacer 12. More preferably, $H_2$ is at least about 80% shorter than distance $H_1$; still more preferably, at least about 90% shorter than $H_1$.

Spacer 30 can be provided by heating spacer 10 up to a temperature at least as high as the deformation temperature of the SMP material and then applying pressure along axis 20 to compress spacer 10 to effectively reduce its volume and/or the cross-sectional area. The deformation temperature can be pre-selected as is described more fully below. In preferred embodiments, the deformation temperature is selected to be above body temperature, but less than a temperature at which adjacent tissue (and organs) can become substantially traumatized and damaged. In preferred embodiments, the deformation temperature is selected to be above about 38° C. and below about 100° C.; more preferably, the deformation temperature is selected to be between about 38° C. and about 65° C.; still yet more preferably, the deformation temperature is selected to be between about 38° C. and about 45° C.

While the forgoing discussion has focused on selecting an SMP material that exhibits an elasticity or super elasticity above a selected temperature, it should be understood that other polymers can be selected for this invention that respond to other stimuli, such as light or radiation, pH changes and chemical/solvent additives. When the selected stimuli is applied to the polymer, the polymer responds, in turn, by a physical change.

Figure 4:
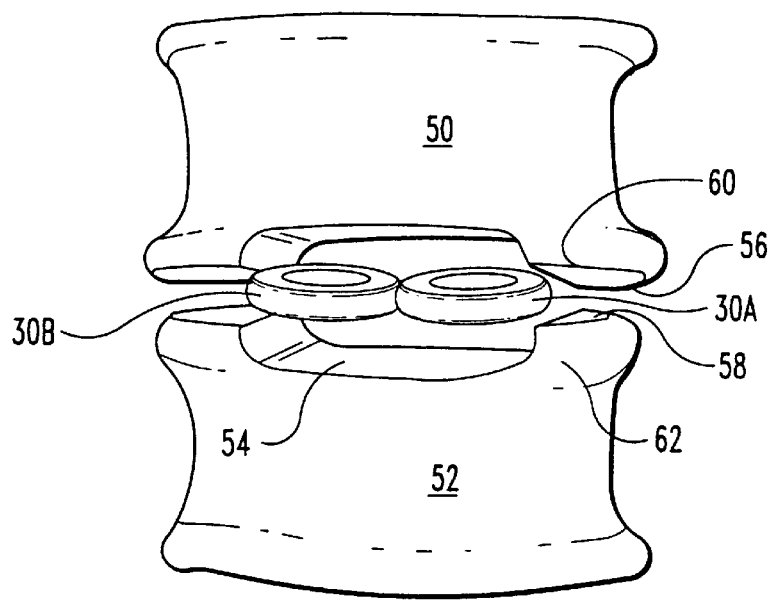
FIG. 4 is a side elevation view illustrating the bi-lateral placement of a pair of deformed spacers according to FIG. 2 implanted in a prepared disc space between adjacent vertebrae.

FIG. 4 illustrates the bi-lateral placement of a pair of spacers 30 of FIG. 2 between adjacent vertebrae 50 and 52. It can be readily seen from the illustrated embodiment that the height of either spacer 30A or 30B is substantially smaller than the height of the prepared disc space 54. Preferably, implantation of either spacer 30A or 30B requires only minimum distraction of the adjacent vertebrae. Furthermore, each of the respective endplates 56 and 58 of vertebrae 50 and 52 only need to be cut to expose the cancellous bone tissue and do not necessarily need to be cut to provide an enlarged opening into disc space 54 for insertion of deformed spacer 30A. While in the illustrated embodiment both endplate 56 of vertebra 50 and endplate 58 of vertebra 52 are illustrated as having their respective cortical rims 60 and 62 cut, it will be understood by those skilled in the art, that it is not necessary to cut the cortical rims 60 and 62 of the respective vertebrae 50 and 52. Furthermore, now providing the substantially intact cortical rim 60 and 62, respectively, effectively inhibits retropulsion of the implanted vertebral spacers 30A and 30B.

Preferably, when spacer 30A rests on lower endplate 58, first surface 14 does not contact upper endplate 56. Thus, spacer 30A can be readily positioned and/or repositioned during surgery to provide optimum efficacy and support. If necessary, spacer 30A can be secured in a desired position by using either temporary or permanent fasteners (not shown), which are commonly used for surgery.

Figure 5:
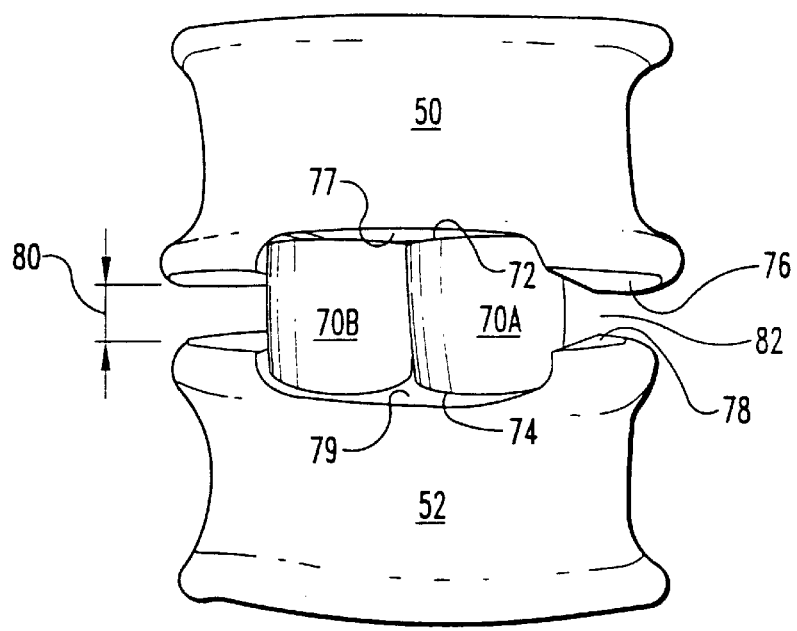
FIG. 5 is a side elevation view illustrating a pair of expanded spacers derived from the spacers of FIG. 4.

Referring additionally now to FIG. 5, it illustrates the expanded vertebral spacers 70A and 70B in disc space 82. Spacers 70A/B are derived from the deformed spacers 30A and 30B, respectively. Spacer 70A will be discussed in more detail with the understanding that the same discussion applies equally to spacer 70B. It is clearly observed from FIG. 5 that upper first surface 72 of spacer 70A bears against the cut portion 77 of the upper endplate 76, while the lower second surface 74 of spacer 70A bears against the cut portion 79 of the lower endplate 78. The expanded vertebral spacer 70A extends from endplate 76 to endplate 78 and maintains the desired disc height and is able to support the weight of the spinal column during normal activities of the patient.

In use, spacers 30A/B are inserted into a prepared disc space. Application of selected stimuli, for example, heating spacers 30A/B to a temperature equal to or above $T_d$, induces the spacers 30A/B to recover their original configuration or a substantially equivalent configuration illustrated as spacers 70A/B. As discussed above, it is preferable that the deformation temperature for the SMP material be selected such that it is sufficiently above the body temperature, yet below a temperature that would injure or traumatize the adjacent tissue surrounding spacers 30A and/or 70B. It is important to have the deformation temperature above body temperature, because above the deformation temperature, the SMP material is elastic and, therefore, can be depressed or deformed by any number of forces. For example, the compressive forces exerted by the spinal column on the spacer itself could cause the spacer to deform into a collapsed or compressed shape. Below the deformation temperature, the SMP material exhibits a substantially rigid configuration and is not readily deformed into other configurations.

In a preferred embodiment, the expanded spacer 70A reverts to the substantially equivalent configuration as that exhibited by the original, molded spacer 10. However, it will be understood that because of the boundary constraints within the prepared disc space 82, spacer 70A may not expand to its full height. Instead, spacer 70A may expand to a height ($H_3$), as represented by reference line 80. It will be understood that the height $H_3$ of spacer 70A may be smaller than the height $H_1$ of spacer 10. In preferred embodiments, height $H_3$ is between about 0.5% and about 20% less than the height $H_1$ of spacer 10.

Advantageously, when spacer 70A does not expand to it full molded height, first surface 72 and second surface 74 bear against the endplates 76 and 78, respectively. Since spacer 70A is above the deformation temperature, the SMP material is sufficiently elastic. The thermodynamic driving force for the SMP material to revert to its original molded configuration is sufficiently high to cause both first surface 72 and second surface 74 to deform or conform to the existing surfaces of the respective endplates 76 and 78. The resulting spacer is formed to matingly engage the respective endplates. This provides an optimal fit in the disc space, decreases the potential for retropulsion of the implanted spacer; and, when the spacer is packed with an osteogenic material, maintains the osteogenic material in intimate contact with the exposed cancellous bone tissue.

Spacer 70A is formed of a body that is composed of a SMP material. Once the SMP material is cooled below the deformation temperature, body 71 is provided in a substantially rigid form that does not deform or compress under the loads exerted by the spinal column. Thus, the SMP material below its deformation temperature exhibits a compression modulus of elasticity between about 2 MPa and about 30 MPa; more preferably, between about 8 MPa and about 15 MPa. As discussed more fully below, the SMP material can be selected from a wide variety of known materials and can include both biodegradable and non-biodegradable materials.

While the forgoing discussion has applied to a pair of identical spacers 70A and 70B, use of two or more unique spacers within the same intervertebral space is included within this invention. For certain orthopedic treatments it may be desirable to use two different spacers. The two spacers can be mirror images of each other. Accordingly, each of the spacers can be provided in a configuration that matingly bears against only a portion of the opposing endplates, for example, a portion of the endplate beginning at the midline of the endplate and extending laterally toward the lateral facet. Alternatively, because of a bone defect, tumor, or diseased bone tissue, the surgeon may desire to combine in a selected vertebral space differently sized spacers or even spacers with a different configuration. (See, for example, the exemplary embodiments of spacers discussed below.)

Figure 6:
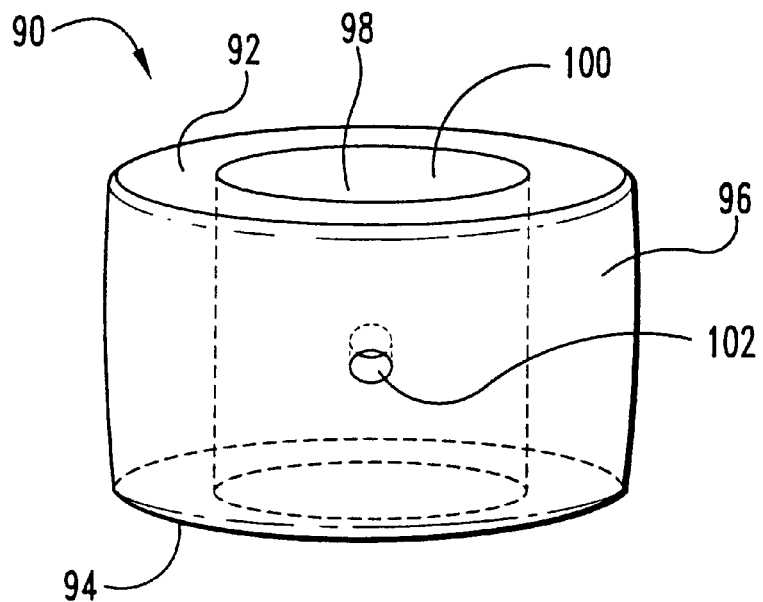
FIG. 6 is a perspective view of an alternative embodiment of a molded spacer for use with the present invention.

FIG. 6 is an illustration of an alternative embodiment of a molded spacer 90 for use in the present invention. Spacer 90 is formed of a SMP material substantially as has been described for spacer 10. Similarly, spacer 90 includes a upper first surface 92, an opposite second surface 94, and a peripheral sidewall 96 therebetween. In the illustrated embodiment, peripheral sidewall 96 includes at least one opening 98 formed therethrough. Spacer 90 can be used to facilitate fusion of the adjacent vertebral bodies. In order to enhance the fusion-promoting capabilities of the spacers of this invention, it is desirable to include with spacer 90 an osteogenic-promoting material. The osteogenic material can be packed in around the spacer, which has been previously inserted in the disc space. It is also preferable to include the osteogenic material inside the internal cavity 100. To facilitate addition of the osteogenic material into cavity 100, sidewall 96 can include at least one opening 102, which can be provided in a wide variety of sizes.

In alternative embodiments, spacer 90 can include a sidewall 96 that does not completely encircle opening 100. Thus, for example, spacer 90 can be formed of a partial cylinder resembling a "C-shape" "J-shape" or a "U-shape". When provided in a partial cylindrical shape, a pair of spacers 90 can be implanted bi-laterally into the disc space such that the internal area 100 of each spacer 90 face each other to form an enlarged interior area. In one form, this would be similar to dividing spacer 90 into two or more portions, which are re-assembled upon implantation into the intervertebral space.

Figure 7:
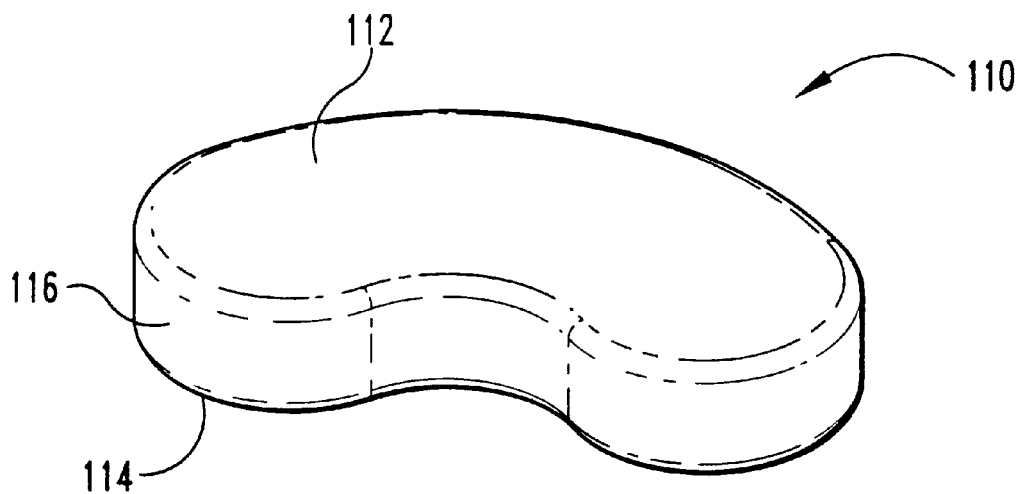
FIG. 7 is a perspective view of a kidney-shaped molded spacer for use with the present invention.

FIG. 7 illustrates yet another embodiment of a deformed spacer 110 for use in this invention. Molded spacer 110 is provided as a substantially solid vertebral spacer that can be implanted into a prepared disc space. It can be seen from the illustrated embodiment that vertebral spacer 110 is provided to substantially resemble a kidney shape or the nucleus pulposa which has been either entirely or partially removed from a discectomy. Before using spacer 110 to repair spinal defects, it is desirable to perform a complete discectomy to remove the entire inner disc and nucleus pulposa, leaving the annulus fibrosis intact. Deformed spacer 110 can be inserted into the prepared disc area. Spacer 110, similar to molded spacer 10, includes an upper surface 112 and an opposite second surface 114 and a sidewall 116 extending therebetween. In a preferred embodiment, spacer 110 is provided to extend laterally across the endplate of a selected vertebra, such as a lumbar vertebra. More preferably, spacer 110 is provided in a size and shape such that when inserted into a prepared disc space, space 110 bears against the cortical rim and/or against the apophysis ring and/or apophyseal bone of each opposing endplate of the adjacent vertebrae. When thus provided, spacer 110 can be provided with a compressive modulus that mimics that of a nucleus pulposa.

Alternatively, spacer 110 can be provided with a compression modulus that more clearly resembles a cortical bone to mimic and/or promote bone fusion between the adjacent vertebrae. Spacer 110 can also include one or more internal cavities and/or openings through sidewall 126 or either bearing surface as described for spacer 90.

Figure 8:
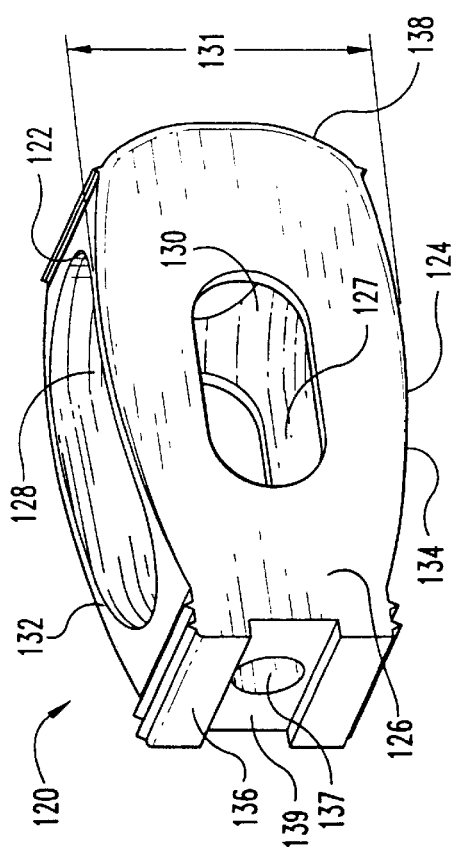
FIG. 8 is a perspective view of yet another embodiment of a molded spacer for use with the present invention.

FIG. 8 illustrates yet another embodiment of a molded spacer 120 for use in the present invention. Molded spacer 120 includes upper first surface 122 and an opposite second surface 124 and a peripheral sidewall 126 extending therebetween. First surface 122 is separated from the second surface by a height represented by reference line 131. Molded spacer 120 also includes a variety of openings into an internal cavity 127. Spacer 120 includes opening 128 in first surface 122 and a corresponding opening in second surface 124 (not shown). In addition, peripheral sidewall 126 can include at least one opening 130.

It can be seen from the illustrated embodiment that upper surface 122 and lower surface 124 define arcuate edges 132 and 134 extending between a first end 136 and a second end 138. In preferred embodiments, first arcuate surface 132 and second arcuate surface 134 are adapted to matingly conform to the opposing endplates of adjacent vertebrae.

Furthermore, first end 138 is presented in a streamlined profile that can be substantially curved or rounded. The streamlined profile of first end 138 further facilitates insertion of a correspondingly deformed spacer (not shown) which can be implanted into a vertebral space. Additionally, second end 136 can include one or more tool-engaging ends 137. In the illustrated embodiment, the tool-engaging end 140 includes a transverse slot 139 extending across second end 136. It will be understood by those skilled in the art that a wide variety of tool-engaging ends can be used to facilitate insertion of a counterpart deformed spacer (not shown) into an intervertebral space.

Figure 9:
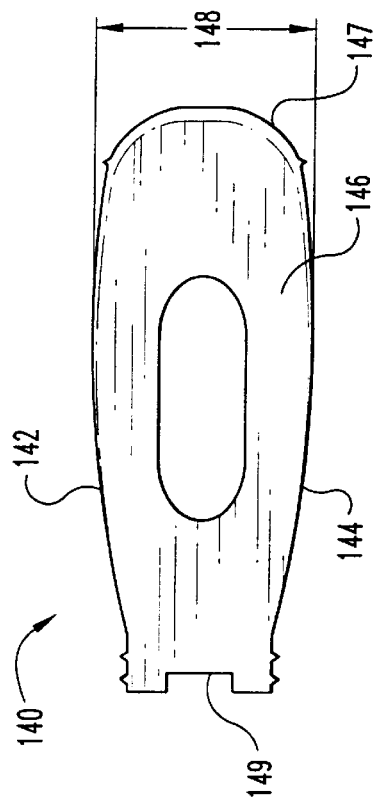
FIG. 9 is a side elevation view of a deformed spacer derived from the spacer of FIG. 8.

FIG. 9 depicts a deformed spacer 140 derived from spacer 120. Accordingly, Spacer 140 comprises a first bearing surface 142, second bearing surface 144 and at least one sidewall 146 therebetween. It can readily be seen from the illustrated embodiment, that the height of spacer 140 represented by reference line 148 is substantially shorter than the corresponding height of spacer 120 (represented by reference line 131). Notably, tool-engaging structures 149 are not distorted to render them ineffective for securing spacer 140 to an insertion tool. Further, the streamlined profile of first end 147 retains a substantial curvature—although defined by a substantially shorter radius than that exhibited by first end 138 of spacer 120.

Figure 11:
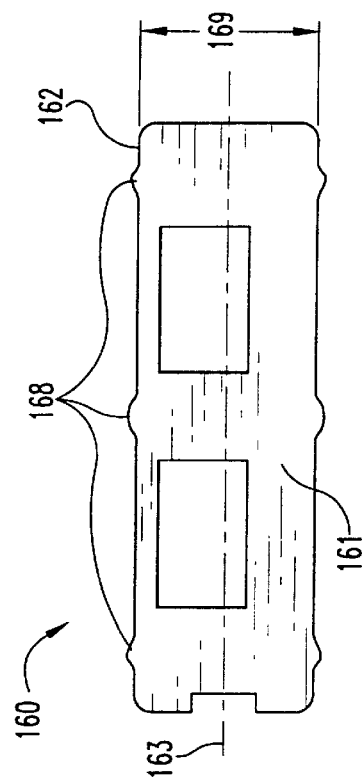
FIG. 11 is a side elevation view of a deformed spacer derived from the spacer of FIG. 9.
Figure 10:
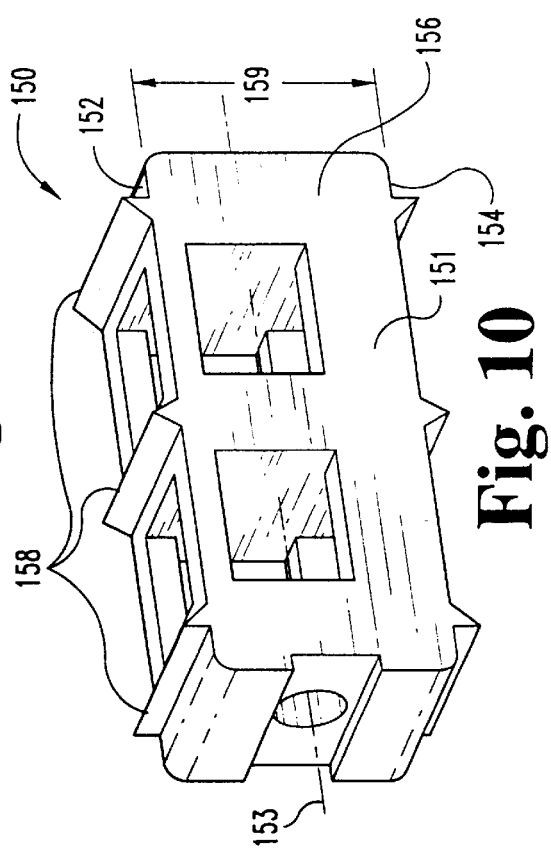
FIG. 10. is a perspective view of yet another embodiment of a molded spacer for use in the present invention.

FIGS. 10 and 11 illustrate still yet another embodiment of a molded spacer 150 and its counterpart deformed spacer 160 for use in the present invention. Spacer 150 comprises an elongated spacer body 151 defining longitudinal axis 153. Similar to the other spacers discussed above, molded spacer 150 includes an upper surface 152 positioned to lie substantially parallel to longitudinal axis 153, a lower surface 154, and a peripheral wall 156 extending therebetween. First surface 152 is separated from second surface 154 by a distance $H_4$ measured orthogonal to axis 153 and illustrated by reference line 159. In the illustrated embodiment, upper surface 152 includes tissue-engaging structures 158. Tissue-engaging structures 158 can be provided to extend up into the cancellous bone tissue of a vertebral body.

Referring specifically to FIG. 11, which illustrates a deformed spacer 160 derived from molded spacer 150. Deformed spacer 160 also comprises elongate body 161 defining a longitudinal axis 163. It can be seen in the illustrated embodiment that body 161 has been compressed orthogonal to axis 163 compared to spacer body 151. Accordingly, deformed body 161 has a substantially reduced height. Therefore, upper surface 162 is separated from lower surface 164 by a distance $H_5$ as illustrated by reference line 169. Comparison of the two spacers reveals that $H_5$ is substantially smaller than $H_4$. It can also be seen that upper surface 162 includes a plurality of projections 168 extending above or proud of surface 162. Upon application of a selected stimuli, such as heating above the deformation temperature, spacer 160 reverts to the molded configuration of spacer 150. In comparing spacers 150 and 160, it can also be observed that peripheral sidewall 166 (of spacer 160) is deformed by exertion of compressive force orthogonal to axis 163.

When deformed, spacer heated to a temperature equal to or greater than $T_d$, the peripheral sidewall reverts or expands to its full extended dimensions or substantially equivalent dimension. During this reversion, projections 168 also revert into tissue-engaging portions 158. Tissue engaging portions 158 can then extend into the cancellous bone tissue. Examples of other expandable spacers are disclosed in co-pending U.S. patent application, Ser. No. 09/696,389, entitled: "Self-Forming Orthopedic Implants," filed on Oct. 25, 2000 (Attorney Docket No. 4002-2500) and U.S. patent application, Ser. No. 09/696,715, filed on Oct. 25, 2000 and entitled, "Laterally Expanding Intervertebral Body Fusion Device", (Attorney Docket No. 4002-2507), both of which are incorporated by reference herein.

Each of the spacers discussed above can be formed of a shaped memory polymeric material. The shaped memory polymeric material can be selected from a wide variety of polymers, including biodegradable and non-biodegradable polymers. In preferred embodiments, the shape memory polymeric material is formed from oligomers, homopolymers, copolymers, and polymer blends that include polymerized monomers derived from 1, d, or d/1 lactide (lactic acid); glycolide (glycolic acid); ethers; olefins, such as ethylene, propylene, butene-1, pentene-1, hexene-1, 4-methylpentene-1, styrene, norbornene and the like; butadiene; polyfunctional monomers such as acrylate, methacrylate, methyl methacrylate; esters, for example, caprolactone, hydroxy buteric acid, hydroxy valeric acid, and mixtures of these monomeric repeating units.

Use of the term copolymers is intended to include within the scope of the invention polymers formed of two or more unique monomeric repeating units. Such copolymers can include random copolymers, graft copolymers, block copolymers, radial block, diblock, triblock copolymers, alternating copolymers, and periodic copolymers. Use of the term polymer blend is intended to include polymer alloys, semi-interpenetrating polymer networks (SIPN) and interpenetrating polymer networks (IPN).

Preferred shape-memory molded spacers of this invention are fabricated to include homopolymers, copolymers, polymer blends, and oligomers of d, 1, d/1 polylactide; polyglycolide, poly(lactide-co-glycolide), poly(β-hydroxy butyrate); polyβ-hydroxy butyrate-co-hydroxyvalerate), (poly(trimethylene carbonate) polyurethane, poly(ethylene-co-vinyl acetate) (EVA), poly(ethylene-co-propylene) (EPR), poly(ethylene-co-propylene-co-diene) ter-polymer (EPDM), poly(ε-caprolactone), poly imino carbonates polyanhydrides, copolymers of ethylene and propylene and/or other α-olefins: or copolymers of these α-olefins. Among them, various types of polyethylene, such as low-density polyethylene, linear low-density polyethylene, medium-density polyethylene and high-density polyethylene, and polypropylene are preferable.

Preferred polymers include biodegradable homopolymers of lactide or glycolide or copolymers thereof. Exemplary polymers are described in U.S. Pat. No. 4,950,258, the entire disclosure of which is incorporated by reference herein. When copolymers of lactide and glycolide are used to form the molded products, the copolymers preferably consist essentially of a composition of 90-10 mol. % lactide and 10-90 mol. % glycolide, and most preferably consist essentially of 80-20 mol. % lactide and 20-80 mol. % of glycolide. Within these specified ranges, the copolymers exhibit desirable deformation characteristics. For example, the copolymers are more pliable and readily deformable at lower temperatures when their mole ratio of lactide and glycolide approximates to 1:1. Generally, the less crystalline phases in the SMP material, the lower the deformation temperature.

The polymer composition of the present invention may further contain thermoplastic resins and/or thermoplastic elastomers to improve its stiffness, moldability and formability. In addition, the shape-memory molded spacer may additionally include additives such as coloring agents, stabilizers, fillers, and the like, in an amount such as will not alter the desired shape-memory effect, biocompatibility and/or biodegradability properties of the molded spacers.

The polymer is characterized in that it will attempt to assume its memory condition by activation of a polymer transition. Activation can occur by adsorption of heat by the polymer, adsorption of liquid by the polymer, or a change in pH in the liquid in contact with the polymer. The polymer is formulated to be responsive to adsorption of a liquid by incorporating in the polymer a hydrophilic material, such an n-vinyl pyrrolidone. Incorporation of a material such as methacrylic acid or acrylic acid into the polymer results in a polymer having a transition that is sensitive to pH. The polymer transition may be a thermally activated transition, where upon adsorption of heat the polymer undergoes a glass transition or a crystalline melting point.

It is also considered to be within the scope of the present invention to provide intervertebral spacers that are formed of a laminate material that comprises one or more layers of a shape memory polymeric material. For example, molded spacer 10 can be provided with an upper surface 12 that includes an exterior layer of a shape memory polymeric material. Similarly, lower surface 14 can also be provided with a laminated layer of a shape memory polymer material. The material used to form the sidewall 16 can be formed of any conventional biocompatible polymeric material. In preferred forms, the peripheral sidewall is formed of a biodegradable polymeric material as has been described above. When thus provided, the laminated spacer can be provided to include a varying compressive modulus depending upon the deformation of the spacer at a constant temperature. For example, a laminated structure where the external layers are formed of a shaped memory polymeric material can have a compressive modulus that is significantly less than the polymeric material used to form the intermediate layer for the peripheral sidewall 114. This provides distinct advantages for spacers by use of the present invention. For example, spacers can have increasing compressive strength to allow greater flexibility of the spine. Alternatively, the laminated structure can provide varying rates of biodegradability in the body. For example, the external laminated layers can be provided in a form having less crystallinity than the intermediate layer for the peripheral sidewall. When polymers such as biodegradable polymers are provided with less crystallinity, they degrade at a much faster rate than polymers that have greater degrees of crystallinity. Polymers with less degree of crystallinity can be prepared by providing copolymers of lactic acid and galactic acid. Increasing the amount of galactic acid in the polymer decreases its crystallinity and therefore increases its rate of degradation.

As mentioned above, the molded spacer can be deformed when heated above its deformation temperature. The deformation temperature ($T_d$) in most situations will be substantially equal to the glass transition temperature ($T_g$). When heated above its deformation temperature, the polymeric material exhibits a elasticity or super elasticity that allows it to be molded into a variety of shapes. For example, for the present invention, the molded spacer can be heated to a temperature between about 40° and about 100° C. Application of a compressive force to deform the spacer into a deformed configuration having a reduced cross-sectional profile can then be applied. The deformed spacer can then be cooled below the $T_d$, which effectively freezes the deformed implant into its deformed configuration. The deformed spacer can used immediately, or the deformed spacer can be stored and/or shipped for use at a later time. Obviously, prior to use, the deformed spacer should be sterilized, preferably using chemical or radiation sterilization techniques.

During surgery, the disc space is prepared to receive the deformed implant. The surgical techniques for partial or full discectomy are commonly known by surgeons skilled in the art. The deformed implant can be inserted from a variety of directions, including posteriorly, anteriorly, or posterior-laterally.

After implantation of the deformed spacer into the prepared disc space, the deformed spacer is then heated above its glass transition temperature. This can be accomplished by a variety of techniques and instrumentations. For example, the deformed spacer can be flushed with warm saline solution, which can then be suctioned out of the patient. Obviously, it is preferable that the warm saline solution be kept at a low enough temperature that it does not traumatize or damage the adjacent tissue. Alternatively, when the spacer includes an opening into its sidewall, the osteogenic material may be heated sufficiently high and thereafter injected into the opening into the peripheral sidewall of the deformed spacer. This can be done in addition to, or instead of, flushing the disc space with warm, sterile saline solution.

In yet another embodiment, a heating tool or other suitable electronic device can be used to heat the implanted deformed spacer without warming and traumatizing the adjacent body tissue. Any suitable heat generating apparatus can be used to heat the SMP material, such as a hot air gun, a small welding or soldering gun, or an electro cautery tip. Also usable are lasers, which are commonly provided in operating rooms. Lasers are especially desirable because they are precise and controlled in their application, can generate sufficient heat very quickly, and cause less thermal necrosis because there is less misdirected heat. The heating operation can be performed in the body during surgery. Still other embodiments include the use of ultra sonic devices, light, and/or other electromagnetic radiation-generating devices.

After the deformed spacer has been heated above its deformation temperature, the deformed spacer automatically undergoes a transition in which it reverts back to its originally molded configuration. However, as has been discussed above, due to spatial constraints within the disc space, the deformed spacer may not be able to obtain the full height ($H_1$) that was originally provided in the originally molded spacer.

When the expanded spacer has been expanded to the desired height, the surgeon can then remove the heat source, thus allowing the expanded spacer to cool down below the deformation temperature and freeze it into its second or expanded confirmation. The spacers will cool to below their deformation temperature in a relatively short time. After the spacers are frozen into their expanded configuration, the surgeon can reduce any distraction that has been applied to the adjacent vertebral bodies. In this expanded confirmation, the implanted spacer has sufficient compressive strength to withstand the biomechanical load exerted by the spinal column.

To further increase the compressive modulus of the spacer, the polymeric material used to form the spacer can include a wide variety of additives such as fillers; binders; reinforcement phases, such as fibers, for example, glass fibers, carbon fibers, and the like; aggregates, for example, ceramic particles or bone derived particles; and platelets.

The spacer can be fabricated by a wide variety of techniques, including injection molding, extrusion molding, vacuum molding, blow molding, and transfer molding. The laminated structures can be fabricated using techniques known in the art including coextrusion, overmolding of the adjacent layers and using biocompatible adhesives to form the laminated structures.

The term osteogenic material used here means virtually any osteo-conductive and/or osteo-inductive material that promotes bone growth or healing, including natural, synthetic and recombinant proteins, hormones, and the like. The osteogenic materials used in this invention preferably comprise a therapeutically effective amount of a bone inductive factor such as a bone morphogenic protein in a pharmaceutically acceptable carrier. Examples of factors include recombinant human bone morphogenic proteins (rhBMPs) rhBMP-2, rhBMP-4 and heterodimers thereof. However, any bone morphogenic protein is contemplated, including bone morphogenic proteins designated as BMP-1 through BMP-13, which are available from Genetics Institute, Inc., Cambridge, Mass. All osteoinductive factors are contemplated whether obtained as above or isolated from bone.

The osteogenic material can include a demineralized bone matrix and, optionally, a carrier, such as a gelatin substance. The demineralized bone matrix can be provided in the form of a powder, paste or gel. When provided as a powder, the osteogenic material can be reconstituted with sterile water, saline, glycerin or other physiological solutions. The reconstituted material is molded about the implant assembly. An osteogenic material can be applied to the intervertebral spacer by the surgeon during surgery or the spacer may be supplied with the composition pre-applied. In such cases, the osteogenic composition may be stabilized for transport and storage. The osteogenic material can be provided as a putty that can be retained in and about the implant assembly. The osteogenic putty is a moldable, flowable material that sets up to a semi-rigid form at about body temperature. The intervertebral spacer with the osteogenic material is then inserted into a prepared disc space. The osteogenic material can also include a reinforcement component such as bone chips, preferably cortical bone chips. Examples of osteogenic material suitable for use with this invention include, but are not limited to: OSTEOFIL, which is commercially available from Regeneration Technologies, Inc. of Alachua, Fla.; GRAFTON CRUNCH available from Osteotech of Eatontown, N.J. and ALLOMATRIX, available from Allosource of Denver, Colo.

The present invention contemplates modifications as would occur to those skilled in the art. It is also contemplated that processes embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An intervertebral spacer for implantation between opposing endplates of adjacent vertebrae, said spacer comprising a body formed from a biodegradable shape memory polymeric material and having an upper first surface, an opposite second surface and a peripheral sidewall extending therebetween, said body provided in a first configuration and capable of deforming under selected stimuli to an expanded second configuration, wherein the upper surface is provided to bear against a first end plate of a first vertebra while the lower surface is provided to bear against a opposing endplate of an adjacent vertebra.

2. The spacer of claim 1 wherein the body is cylindrical.

3. The spacer of claim 1 wherein the body is kidney shaped.

4. The spacer of claim 1 wherein the body is C-shaped.

5. The spacer of claim 1 wherein the body is an elongate body having a longitudinal axis positioned to lie substantially parallel to the first surface.

6. The spacer of claim 1 wherein the body includes an interior cavity for receipt of an osteogenic material.

7. The spacer of claim 1 wherein at least one of the sidewall, first surface and the second surface has at least one opening extending therethrough.

8. The spacer of claim 1 wherein the stimuli includes thermal or photoradiation energy.

9. The spacer of claim 1 wherein the selected stimuli includes heating to a deformation temperature greater than about 37° C.

10. The spacer of claim 9 wherein the body at a temperature below the deformation temperature exhibits a compression modulus comparable to that of cortical bone.

11. The spacer of claim 1 wherein the stimuli includes heating to a deformation temperature between about 40° C. and about 100° C.

12. The spacer of claim 11 wherein the deformation temperature is between about 40° C. and about 65° C.

13. The spacer of claim 1 wherein the polymeric material is a thermoplastic.

14. The spacer of claim 1 wherein the shaped memory polymeric material is selected from the group consisting of: polylactide, polyglycolide, poly(lactide-co-glycolide), poly($\epsilon$-caprolactone), poly($\beta$-hydroxybutyrate), poly($\beta$- hydroxybutyrate-co-hydroxyvalerate), and mixtures, copolymers and blends thereof.

15. The spacer of claim 1 wherein the body is adapted to withstand 500 Newtons compressive force without significant deformation when maintained below the deformation temperature.

16. The spacer of claim 1 wherein the peripheral sidewall comprises a first lateral wall portion, a second lateral wall portion and an end wall portion therebetween.

17. The spacer of claim 1 wherein said body deforms to said second configuration upon implantation in an intervertebral disc space.

18. The spacer of claim 7 wherein in the second configuration, said first bearing surface conforms to an opposing endplate of a first vertebra and said second bearing surface conforms to an opposing endplate of an second vertebra adjacent to said first vertebra.

19. An intervertebral spacer for implantation between adjacent vertebrae, said spacer comprising a body comprising a first bearing surface, an opposite second bearing surface, and a peripheral sidewall therebetween and composed of a biodegradable, shape memory polymeric material, said body capable of withstanding a compressive force of at least 500 Newtons without significant deformation when maintained at a temperature below a deformation temperature, yet capable of deforming above the deformation temperature.

20. The spacer of claim 19 wherein the body is cylindrical.

21. The spacer of claim 19 wherein the body is kidney shaped.

22. The spacer of claim 19 wherein the body is C-shaped.

23. The spacer of claim 19 wherein the body is an elongate body having a longitudinal axis positioned to lie substantially parallel to the first surface.

24. The spacer of claim 19 wherein the body includes an interior cavity for receipt of an osteogenic material.

25. The spacer of claim 19 wherein at least one of the sidewalls, the first surface and the second surface has at least one opening extending therethrough.

26. The spacer of claim 19 wherein the stimuli includes thermal or photoradiation energy.

27. The spacer of claim 19 wherein the stimuli includes heating to a deformation temperature between about 40° C. and about 100° C.

28. The spacer of claim 27 wherein the deformation temperature is between about 40° C. and about 65° C.

29. The spacer of claim 19 wherein the polymeric material is a thermoplastic.

30. The spacer of claim 19 wherein the shaped memory polymeric material is selected from the group consisting of: polylactide, polyglycolide, poly(lactide-co-glycolide), poly($\epsilon$-caprolactone), poly($\beta$-hydroxybutyrate), poly($\beta$-hydroxybutyrate-co-hydroxyvalerate), and mixtures, copolymers and blends thereof.

31. A method of orthopedic treatment, said method comprising:

preparing a disc space between adjacent vertebrae to receive a spacer to receive an intervertebral spacer, implanting an intervertebral spacer in the prepared disc space, said spacer composed of a biodegradable, shape memory polymeric material and provided in a first configuration exhibiting a first external volume, and subjecting said spacer to a selected stimuli wherein said spacer deforms to a second configuration exhibiting a second external volume greater than the first external volume.

32. The method of claim 31 wherein said subjecting comprises subjecting the spacer to a selected stimuli after the spacer has been implanted into the prepared disc space.

33. The method of claim 31 wherein the selected stimuli comprises heating the spacer to a temperature between about 40° C. and about 60° C.

34. The method of claim 31 wherein the body is cylindrical.

35. The method of claim 31 wherein the body is kidney shaped.

36. The method of claim 31 wherein the body is C-shaped.

37. The method of claim 31 wherein the body is an elongate body having a longitudinal axis positioned to lie substantially parallel to the first surface.

38. The method of claim 31 wherein the body includes an interior cavity for receipt of an osteogenic material.

39. The method of claim 31 comprising contacting the endplates with osteogenic material to promote spinal fusion.

* * * * *